United States Patent
Heid et al.

(10) Patent No.: US 12,405,263 B2
(45) Date of Patent: Sep. 2, 2025

(54) METHOD FOR THE QUANTITATIVE DETERMINATION OF Al4C3 AND APPARATUS FOR CARRYING OUT THE METHOD

(71) Applicant: REFRACTORY INTELLECTUAL PROPERTY GMBH & CO. KG, Vienna (AT)

(72) Inventors: Stefan Heid, Leoben (AT); Roland Nilica, Sankt Marein-Feistritz (AT); Markus Ellersdorfer, Leoben (AT); Stefan Niedermayer, Leoben (AT)

(73) Assignee: REFRACTORY INTELLECTUAL PROPERTY GMBH & CO. KG, Vienna (AT)

( * ) Notice: Subject to any disclaimer, the term of this patent is extended or adjusted under 35 U.S.C. 154(b) by 165 days.

(21) Appl. No.: 18/251,539

(22) PCT Filed: Oct. 28, 2021

(86) PCT No.: PCT/EP2021/080052
§ 371 (c)(1),
(2) Date: May 2, 2023

(87) PCT Pub. No.: WO2022/117268
PCT Pub. Date: Jun. 9, 2022

(65) Prior Publication Data
US 2024/0011968 A1    Jan. 11, 2024

(30) Foreign Application Priority Data

Dec. 4, 2020   (EP) .................... 20211921

(51) Int. Cl.
*G01N 33/38*    (2006.01)

(52) U.S. Cl.
CPC ................... *G01N 33/388* (2013.01)

(58) Field of Classification Search
None
See application file for complete search history.

(56) References Cited

U.S. PATENT DOCUMENTS

| 5,214,203 A | * | 5/1993 | Koyama | C07C 51/12 |
| | | | | 560/232 |
| 7,966,971 B2 | * | 6/2011 | Zimmerman | A01K 5/0225 |
| | | | | 119/51.02 |

FOREIGN PATENT DOCUMENTS

| CN | 104931604 A | | 9/2015 |
| CN | 210058561 U | * | 2/2020 |
| CN | 210512616 U | * | 5/2020 |
| CN | 211921570 U | * | 11/2020 |
| DE | 112009004278 T5 | | 9/2012 |
| JP | S62198757 A | | 2/1987 |
| JP | 2016155096 A | | 9/2016 |

(Continued)

OTHER PUBLICATIONS

Simensen, Christian J., "Gas-Chromatographic Analysis of Carbides in Aluminium and Magnesium", In Fresenius Z. Anal. Chem., vol. 292, 1978, pp. 207-212.

(Continued)

*Primary Examiner* — Daniel S Larkin
(74) *Attorney, Agent, or Firm* — CALFEE, HALTER & GRISWOLD LLP

(57) ABSTRACT

The invention relates to a method for quantitatively determining $Al_4C_3$ and a device for carrying out the method.

9 Claims, 3 Drawing Sheets

(56) References Cited

FOREIGN PATENT DOCUMENTS

WO      2010071196 A1    6/2010
WO      2022117268 A1    6/2022

OTHER PUBLICATIONS

Favre, et al., "Reaction Between Liquid Al (or Si) and Composite C/C Materials", In High Temperature Ceramic Matrix Composites, International Conference on High Temperature Ceramic Composites, Oct. 12, 2001, pp. 334-340.

Edtmaier, et al., "Microstructural Characterization and Quantitative Analysis of the Interfacial Carbides in Al(Si)/ diamond Composites", In Journal of Material Science, vol. 53, No. 22, Jul. 30, 2018, pp. 15514-15529.

Siegenthaler, et al., "Conversion of Water to a Counting Gas for Low-Level Tritium Measurements by Means of Aluminium Carbide", In International Journal of Applied Radiation and Isotopes, vol. 26, No. 8, Aug. 1, 1975, pp. 459-464.

Nandy, et al., "Hydration of Coked MgO—C—Al Refractories", In Ceramics International, Elsevier, vol. 32, No. 2, Apr. 25, 2005, pp. 163-172.

Office Action for Korean Application No. 10-2023-7015345 (Machine Translation included), dated Nov. 1, 2024, 8 pages.

Office Action from Japanese Application No. 2023-523629 dated Mar. 28, 2024, 7 pages (German translation included).

\* cited by examiner

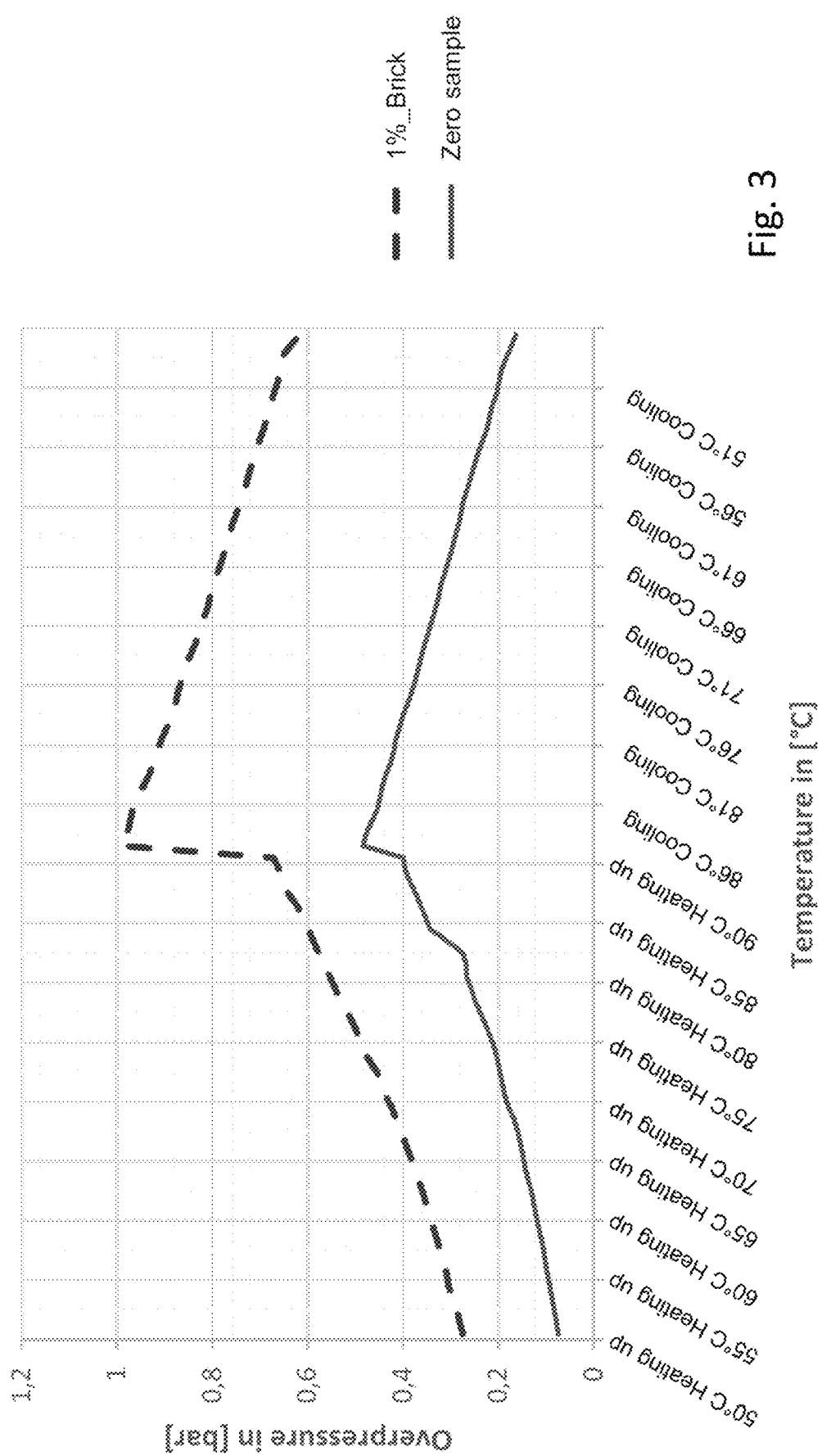

METHOD FOR THE QUANTITATIVE DETERMINATION OF Al4C3 AND APPARATUS FOR CARRYING OUT THE METHOD

CROSS-REFERENCE TO RELATED APPLICATIONS

This application is a United States National Stage Entry of PCT/EP2021/080052, filed on Oct. 28, 2021, and entitled "METHOD FOR QUANTITATIVELY DETERMINING $Al_4C_3$ AND DEVICE FOR CARRYING OUT THE METHOD", which claims priority to European Patent Application No. EP20211921.0, filed on Dec. 4, 2020. The entireties of these applications are incorporated herein by reference.

BACKGROUND

The invention relates to a method for the quantitative determination of $Al_4C_3$ and an apparatus for carrying out the method.

$Al_4C_3$ is an aluminum carbide which is formed as a reaction product of aluminum (Al) and carbon (C), in particular at high temperatures.

$Al_4C_3$ has the property of reacting in the presence of water, for example in the form of liquid water or atmospheric moisture, to form aluminum hydroxide and methane. This can cause problems when products comprising $Al_4C_3$ are in a humid environment.

A typical problem is the presence of $Al_4C_3$ in refractory products. $Al_4C_3$ can form in substantial proportions, particularly in carbon-bonded refractory products to which aluminum is added as an antioxidant. During the use of these refractory products at high temperatures, $Al_4C_3$ is formed from carbon and aluminum. To the extent that these refractory products are permanently exposed to elevated temperatures after the formation of $Al_4C_3$, the presence of $Al_4C_3$ in the refractory product is regularly not problematic. However, $Al_4C_3$ can become problematic, for example, if such used refractory products are used as recycled raw material for the production of new refractory products after their use. This is because during the production or storage of such a recycled refractory raw material or of a new refractory product manufactured from it, the $Al_4C_3$ can hydrate with moisture, for example from the ambient air, and, due to the volume expansion associated with this, lead to damage or even destruction of the new refractory product.

However, to the extent that $Al_4C_3$ is present only in small proportions in a refractory product, $Al_4C_3$ is usually tolerable. At the same time, there is a need to use used refractory products comprising $Al_4C_3$ as a recycled raw material for the production of new refractory products. Therefore, in order to be able to determine the amount of $Al_4C_3$ introduced into a new refractory product by a recycled raw material, it is necessary to be able to quantitatively determine the amount of $Al_4C_3$ in the used refractory product to be used as a recycled raw material.

SUMMARY

The invention is based on the task to provide a method for the quantitative determination of $Al_4C_3$. In particular, it is intended to provide such a method for the reliable quantitative determination of $Al_4C_3$. In particular, such a method for the reliable, simple and safe quantitative determination of $Al_4C_3$ is to be provided.

A further object of the invention is to provide an apparatus for carrying out such a method.

To solve the problem, according to the invention, there is provided a method for the quantitative determination of $Al_4C_3$, comprising the following steps:
 providing a gas-tight sealable chamber;
 providing a substance comprising $Al_4C_3$, wherein the substance comprising $Al_4C_3$ is provided in the form of a refractory product;
 providing at least one aqueous liquid that reacts with Al4C3 to form at least one gas;
 placing the substance comprising $Al_4C_3$ and the at least one aqueous liquid in the chamber;
 sealing the chamber in a gas-tight manner;
 reacting the $Al_4C_3$ of the substance comprising $Al_4C_3$ and the at least one aqueous liquid in the chamber to form the at least one gas;
 quantitatively determining the at least one gas formed; and
 quantitatively determining Al4C3 in the substance comprising Al4C3 based on the quantitative determination of the at least one gas formed.

The invention is based on the surprising finding that such a method can provide a particularly reliable, simple and safe method for the quantitative determination of $Al_4C_3$. In particular, the invention is also based on the surprising finding that the method can be carried out in a particularly reliable, simple and safe manner, in particular also due to the use of the aqueous liquid as well as the gas-tight sealing of the chamber.

According to the method of the invention, the proportion of $Al_4C_3$ in the substance comprising $Al_4C_3$ is not determined directly. Rather, the at least one gas formed by the reaction of the $Al_4C_3$ of the substance comprising $Al_4C_3$ and the at least one aqueous liquid in the chamber is quantitatively determined, and the proportion of $Al_4C_3$ in the substance comprising $Al_4C_3$ is indirectly quantitatively determined based on the quantitative determination of the formed at least one gas.

Preferably, when carrying out the method according to the invention, the substance comprising $Al_4C_3$ and the at least one aqueous liquid are first arranged in the chamber and the chamber is then sealed in a gas-tight manner. Subsequently, the $Al_4C_3$ of the substance comprising $Al_4C_3$ and the at least one aqueous liquid in the chamber are allowed to react with each other to form the at least one gas. Preferably, the chamber remains sealed in a gas-tight manner during this reaction. In particular, the chamber preferably remains sealed gas-tight until the substance comprising $Al_4C_3$ and the at least one aqueous liquid in the chamber have completely reacted with each other to form the at least one gas. Subsequently, that is, after the reaction of the $Al_4C_3$ of the substance comprising $Al_4C_3$ and the at least one aqueous liquid in the chamber to form the at least one gas, the formed at least one gas is quantitatively determined. Preferably, the at least one gas formed is quantitatively determined after the reaction is complete, that is, after the $Al_4C_3$ of the substance comprising $Al_4C_3$ and the at least one aqueous liquid in the chamber have completely reacted with each other to form the at least one gas. Depending on the method used for the quantitative determination of the formed at least one gas, after the reaction of the substance comprising $Al_4C_3$ and the at least one aqueous liquid in the chamber to form the at least one gas, the chamber may either be opened or remain closed in a gas-tight manner for the quantitative determination of the formed at least one gas. Subsequently, that is, after the quantitative determination of the formed at least one gas, the $Al_4C_3$ in the substance comprising $Al_4C_3$ is quantitatively determined based on the quantitative determination of the formed at least one gas.

According to a particularly preferred embodiment, the at least one gas formed during the reaction of the $Al_4C_3$ of the substance comprising $Al_4C_3$ and the at least one aqueous liquid in the chamber is methane. As is known, $Al_4C_3$ reacts with water to form aluminum hydroxide and methane according to the following reaction equation (I):

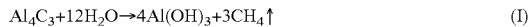
$$Al_4C_3 + 12H_2O \rightarrow 4Al(OH)_3 + 3CH_4\uparrow \qquad (I)$$

In carrying out the process according to the invention, the $Al_4C_3$ of the substance comprising $Al_4C_3$ reacts with the at least one aqueous liquid in the chamber according to the above reaction equation (I) to form aluminum hydroxide and gaseous methane. Therefore, based on the quantitative determination of the gaseous methane formed in the process, the proportion of $Al_4C_3$ in the substance comprising $Al_4C_3$ can be quantitatively determined very accurately.

For the quantitative determination of the at least one gas formed, i.e., preferably the methane, it is possible in principle to use the methods known from the prior art for the quantitative determination of gases, in particular for the quantitative determination of methane.

For example, the quantitative determination of the at least one gas can be carried out by means of a gas analytical determination. In this case, the at least one gas is quantitatively determined by means of the known gas-analytical measurement methods. For example, based on the measurement of the concentration of the at least one gas in the chamber, the at least one gas can be quantitatively determined. For this purpose, for example, the concentration of the at least one gas formed in the chamber may be measured in a gas volume and further the gas volume may be measured and based on these measurements the at least one gas may be quantitatively determined. For example, the at least one gas formed in the chamber may be introduced into a gas volume and the concentration of the at least one gas in the gas volume may be measured and further the gas volume may be measured and based on these measurements the at least one gas may be quantified. Preferably, the concentration of the at least one gas can be measured by means of a gas sensor. Preferably, the gas sensor is an infrared optical gas sensor. By means of such an infrared-optical gas sensor (in particular an NDIR), the concentration of the at least one gas can be determined by measuring the optical transmission of the gas in a spectral range characteristic for the gas. From this, the concentration of the at least one gas can be determined using Lambert-Beer's law. The gas volume can be determined, for example, by a flow meter. Such a gas-analytical quantitative determination is explained in more detail below in the embodiment example.

For example, the quantitative determination of the at least one gas can alternatively be performed based on a pressure measurement. In this case, the pressure in the chamber resulting from the reaction of the substance comprising $Al_4C_3$ with the at least one aqueous liquid in the chamber is measured and, based on this measurement, the at least one gas is quantitatively determined. The pressure can preferably be determined by means of a pressure sensor. Such quantitative determination of the at least one gas by means of pressure measurement is also explained in more detail below in the embodiment example.

Based on the quantitative determination of the at least one gas formed, the quantitative determination of $Al_4C_3$ in the substance comprising $Al_4C_3$ can then be performed. Here, on the basis of the knowledge of the reaction equation according to which the at least one gas is formed during the reaction of the $Al_4C_3$ of the substance comprising $Al_4C_3$ and the at least one aqueous liquid in the chamber, the amount of $Al_4C_3$ in the substance comprising $Al_4C_3$ can be quantitatively determined or calculated, in particular by means of a stoichiometric calculation.

For example, insofar as according to the above reaction equation (I) the $Al_4C_3$ of the substance comprising $Al_4C_3$ reacts with the at least one aqueous liquid in the chamber to form a gas in the form of methane, the quantitative determination of the methane formed allows the amount of $Al_4C_3$ to be easily quantitatively determined by a stoichiometric calculation. This is because, according to the reaction equation (I), one mole of $Al_4C_3$ reacts to form 3 moles of gaseous methane in the presence of water in each case. Accordingly, by quantitatively determining the gaseous methane formed, the amount of $Al_4C_3$ can be quantitatively determined. Such quantitative determination of $Al_4C_3$ is explained in more detail below in the embodiment example.

Surprisingly, it has been found in the context of the invention that the method according to the invention can be carried out particularly simply, reliably and safely, insofar as the substance comprising $Al_4C_3$ is allowed to react with an aqueous liquid. For the purposes of the invention, an aqueous liquid is understood to mean a liquid comprising water, in particular a water-based liquid. According to a particularly preferred embodiment, the aqueous liquid is in the form of water. According to a particularly preferred embodiment, the aqueous liquid, in particular a water-based liquid, is pH-neutral or at least substantially pH-neutral. In this respect, the aqueous liquid preferably has a pH in the range from 6 to 8 and particularly preferably a pH of 7.

An essential advantage of such an aqueous liquid is that $Al_4C_3$ reacts in the presence of such an aqueous liquid according to the above reaction equation (I) to form methane, and the proportion of $Al_4C_3$ can be quantitatively determined via the quantitative determination of the methane formed in the process. This results in a particularly reliable and simple quantitative determination of $Al_4C_3$.

A further significant advantage of such an aqueous liquid is that such an aqueous liquid, in particular water or a pH-neutral aqueous liquid, is particularly easy to handle, since such a liquid does not endanger the operating personnel when carrying out the process according to the invention and also does not exert an aggressive influence on the apparatus for carrying out the process according to the invention.

Another advantage of such an aqueous liquid is that such an aqueous liquid is advantageous from an ecological point of view.

A further advantage of such an aqueous liquid is that such an aqueous liquid is advantageous from an economic point of view, since it can be provided at low cost.

The substance comprising $Al_4C_3$ provided for the process according to the invention can in principle be any substance comprising $Al_4C_3$. The substance comprising $Al_4C_3$ is preferably carbon-bonded. According to a particularly preferred embodiment, the substance comprising $Al_4C_3$ is provided in the form of a refractory product. As stated above, the quantitative determination of the proportion of $Al_4C_3$ in refractory products is of particular importance, for example insofar as these are to be used as recycled raw material for the production of new refractory products. The method according to the invention thus provides a method by which the proportion of $Al_4C_3$ in such refractory products can be determined particularly simply, reliably and safely. According to a preferred embodiment, the refractory product is a carbon-bonded refractory product, particularly preferably a used carbon-bonded refractory product.

By the term "carbon bonded" it is preferably meant that the substance comprising $Al_4C_3$, preferably the substance comprising $Al_4C_3$ in the form of a refractory product, is bonded via a carbon bond. This carbon bond can be formed by adding a carbon-containing binder during the production of the substance. The carbon-containing binder may be, for example, pitch or a synthetic resin, preferably a phenolic resin. By a "phenolic resin" is meant a synthetic resin formed from a phenol or a phenol derivative and an aldehyde.

"Used" in this sense means that the product has already been used for its intended purpose. Such a carbon-bonded refractory product may particularly preferably be a magnesia carbon brick, especially a used magnesia carbon brick. As is well known, magnesia-carbon bricks are refractory products consisting mainly of carbon (C) and magnesia (MgO). Such bricks are also referred to as MgO—C bricks. In such a magnesia-carbon brick, the magnesia is preferably bonded together by a carbon bond. Preferably, the magnesia carbon brick provided for carrying out the process according to the invention, in particular used magnesia carbon brick, comprises a proportion of carbon of 5-30% by mass, a proportion of magnesia of 70-95% by mass and a proportion of $Al_4C_3$ of 0-3% by mass, in each case based on the total mass of the magnesia carbon brick. In addition, the magnesia carbon brick optionally comprises proportions of metals (in particular silicon and aluminum) and nitrides, in particular aluminum nitrides.

The method according to the invention proves to be particularly advantageous for the quantitative determination of $Al_4C_3$ in such used magnesia carbon bricks, in particular also from an ecological and economic point of view, since up to now no reliable, simple and safe method has been available for this purpose. As a result, used magnesia carbon bricks could often not be reused as recycled pipe material due to a proportion of $Al_4C_3$ that could not be quantitatively determined.

According to a preferred embodiment, it is provided that the substance comprising $Al_4C_3$ is provided as bulk material. Bulk material in this sense refers to a pourable material consisting of particles or grains. Preferably, the grains of the bulk material have a grain size below 10 mm, even more preferably below 5 mm.

A particular advantage of such a substance comprising $Al_4C_3$ provided as bulk material is that the $Al_4C_3$ of such a substance comprising $Al_4C_3$ provided as bulk material can react completely with the aqueous liquid, so that a particularly reliable quantitative determination of the proportion of $Al_4C_3$ is possible.

According to a particularly preferred embodiment, it is provided that temperature is applied to the chamber during the reaction of the substance comprising Al4C3 with the at least one aqueous liquid in the chamber. In particular, it may be provided to apply temperature to the chamber at a temperature above room temperature, i.e., above 20° Celsius. Preferably, it is provided to apply temperature to the chamber at temperature above 100° Celsius and particularly preferably at & temperature in the range of 100°-200° Celsius. In principle, the chamber can be acted upon with temperature by any means known in the prior art for acting upon a chamber with temperature. Preferably, temperature is applied to the room by means of an electric heating device.

According to the invention, it has been found that applying temperature to the chamber has several advantages. One advantage is that the reaction of the substance comprising $Al_4C_3$ with the at least one aqueous liquid can be accelerated. This allows the process according to the invention to be carried out particularly quickly and efficiently. However, a further particular advantage of subjecting the chamber to temperature is in particular also that, by subjecting the chamber to temperature, such a defined atmosphere can be set in the chamber that one or more gases of the at least one gas which form during the reaction of the substance comprising $Al_4C_3$ of the $Al_4C_3$ with the at least one aqueous liquid in the chamber are in the gas phase, which enables the process according to the invention to be carried out particularly simply. Because hereby, by quantitatively determining these formed gases which are in the gaseous phase at the atmosphere set above the temperature in the room, the proportion of the $Al_4C_3$ of the substance comprising $Al_4C_3$ can be particularly easily quantitatively determined on the basis of this quantitative determination of the formed at least one gas.

Which gases are in the gas phase in a set atmosphere in the chamber can be determined and set by the known gas equations.

According to a preferred embodiment, it is provided that the chamber is under overpressure during the reaction of the substance comprising $Al_4C_3$ with the at least one aqueous liquid in the chamber. Overpressure in this sense means pressure above atmospheric pressure, i.e. a pressure above 1 bar. Preferably, an overpressure in the range of 2-6 bar, more preferably 3-5 bar, prevails in the chamber during the reaction.

Such an overpressure can occur during the reaction of the substance comprising $Al_4C_3$ with the at least one aqueous liquid in the chamber while the latter is sealed gas-tight and, in particular, is subjected to temperature. In this respect, no additional technical measures are necessary to pressurize the chamber accordingly.

According to the invention, it has been found that such an overpressure in the chamber during the reaction is associated with numerous advantages. Firstly, it has been surprisingly found in this respect that the reaction proceeds more rapidly, so that the reaction time can be shortened and the process can thus be carried out particularly quickly and effectively. Furthermore, however, it is also advantageous in particular that, as stated above, by applying temperature and overpressure to the chamber, such a defined atmosphere can be set in the chamber that defined gases are present in the gas phase, which, as stated above, enables a particularly simple quantitative determination of the at least one gas formed and, on this basis, also a particularly simple quantitative determination of $Al_4C_3$ in the substance comprising $Al_4C_3$.

According to a particularly preferred embodiment, the chamber is provided by an autoclave. As is known, an autoclave is a device comprising a gas-tight sealable chamber in which substances can be subjected to temperature at overpressure. The process according to the invention can therefore be carried out particularly advantageously in an autoclave, since an autoclave not only provides a gas-tight sealable chamber, but this chamber can also be subjected to temperature and overpressure.

A further particular advantage of the use of an autoclave for carrying out the method according to the invention is in particular also that, to this extent, for carrying out the method according to the invention, recourse can be had to a device according to the prior art in order to carry out the method according to the invention. The method according to the invention can thus be carried out particularly easily with the aid of an autoclave.

It is also an object of the invention to provide an apparatus for carrying out the method according to the invention, comprising:
- a gas-tight sealable chamber; and
- means for quantitative determining gas formed in the chamber.

The gas-tight sealable chamber can preferably be provided by an autoclave, as set forth above.

The means for quantitative determination of gas formed in the chamber preferably comprise at least one of the following means: an infrared-optical gas sensor or a pressure sensor.

Further features of the invention will be apparent from the claims, the figures and the accompanying figure description.

All features of the invention may be combined, individually or in combination, in any desired manner.

Examples of embodiments of the invention are described in more detail below with reference to the accompanying figures.

BRIEF DESCRIPTION OF THE DRAWINGS

FIG. 3 shows measurement results for the pressure measurement when carrying out the exemplary embodiment of the method according to the invention.

DETAILED DESCRIPTION

Exemplary Embodiment of the Apparatus

Figure 1:
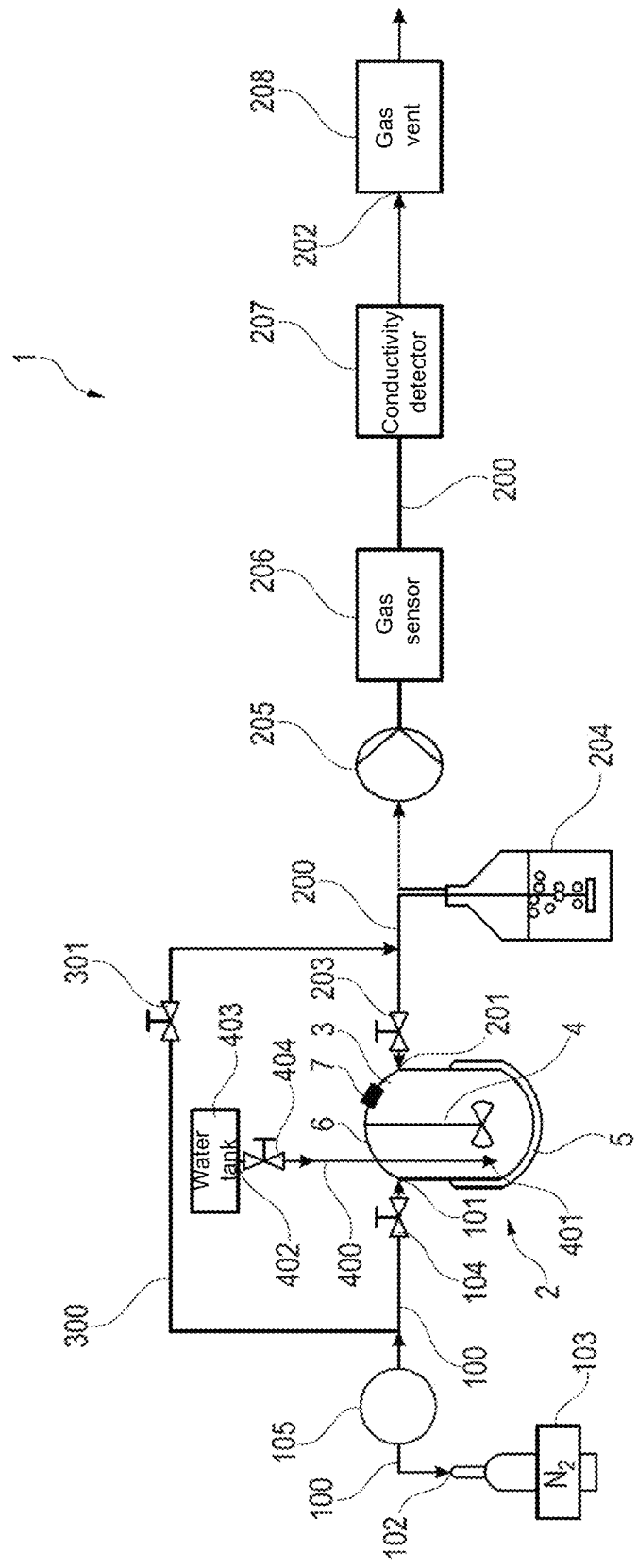
FIG. 1 shows a highly schematized embodiment of an apparatus for carrying out the method according to the invention.

In its entirety, the apparatus in FIG. 1 is designated with the reference sign 1.

The apparatus 1 comprises an autoclave 2, which comprises a chamber 3 that can be sealed in a gas-tight manner. The autoclave 2 further comprises a stirrer 4, by means of which substances present in the chamber 3 can be stirred and mixed, and an electrical heating device for applying temperature to the chamber 3. The autoclave 2 has a lid 6, by means of which the chamber 3 can be sealed in a gas-tight manner. The autoclave 2 further has a pressure sensor 7 for measuring the pressure in the chamber 3.

A first gas conduit 100 is guided through the wall of the autoclave 2 and extends from a first end 101, at which the first gas conduit 100 opens into the chamber 3, to a second end 102. At its second end 102, the first gas conduit is connected to a nitrogen tank 103 containing nitrogen. A first gas conduit path is defined by the first gas conduit 100, through which gas can be conducted along the first gas conduit 100 from the second end 102 to the first end 101. The first gas conduit 100 can be closed by a valve 104.

A second gas conduit 200 is passed through the wall of the autoclave 2, extending from a first end 201, where the second gas conduit 200 opens into the chamber 3, to a second end 202. A second gas conduit path is defined by the second gas conduit 200, through which gas can be conducted along the second gas conduit 200 from the first end 201 to the second end 202. Along the second gas conduit 200, in the direction of flow of the second gas conduit path from the first end 201 to the second end 202, the following components are arranged: A valve 203, a gas wash bottle 204 arranged fluidically therebehind, a gas conditioning pump 205 arranged fluidically therebehind, a gas sensor 206 arranged fluidically therebehind, and a conductivity detector 207 arranged fluidically therebehind. Finally, the second gas conduit 200 opens into a gas vent 208 at the second end 202 arranged fluidically downstream of the conductivity detector 207. The second gas conduit 200 can be shut off by the valve 203. The gas wash bottle 204 includes a bath of 10% sulfuric acid through which the second gas conduit path is passed. A gas flowing along the second gas conduit path is coolable to 5° C. by the gas conditioning pump 205. To control the gas flow rate along the second gas conduit path downstream of the gas conditioning pump 205, the gas volume flow rate through the gas conditioning pump 205 can be adjusted. The gas sensor 206 is an infrared optical gas sensor, through which the concentration of gaseous methane conducted along the second gas conduit path can be measured. The conductivity detector 207 is a thermal conductivity detector through which the concentration of gaseous hydrogen conducted along the second gas conduit path is measurable.

A third gas conduit 300 extends from a portion of the first gas conduit 100 between the second end 102 and the valve 104 to a portion of the second gas conduit 200 between the valve 203 and the gas wash bottle 204. A third gas conduit path is defined by the third gas conduit 300, through which gas can be conducted along the third gas conduit 300 from the protruding portion of the first gas conduit to the protruding portion of the second gas conduit 200. The third gas conduit 300 can be closed by a valve 301.

On the conduit portion of the first gas conduit 100 between the nitrogen tank 103 and the branch of the first gas conduit 100 into the third gas conduit 300, the first gas conduit 100 includes a flow meter 105 for measuring the volume of gas of nitrogen gas flowing through the first gas conduit 100.

A fourth conduit 400 is routed through the lid 6 of the autoclave 2, extending from a first end 401, where the fourth conduit 400 opens into the chamber 3, to a second end 402. At its second end 402, the fourth conduit is connected to a water tank 403 containing water. A conduit path is defined by the fourth conduit 400, through which water can be conducted along the fourth conduit 400 from the second end 402 to the first end 401. The fourth conduit 400 can be closed by a valve 404.

Exemplary Embodiment of the Method

In a practical application, according to a first exemplary embodiment, the method according to the invention is carried out on the apparatus 1 as follows, wherein the quantitative determination of the formed at least one gas, in the exemplary embodiment methane, is carried out by means of a gas analytical quantitative determination of the methane.

The aforementioned apparatus 1 is provided. By means of the autoclave 2, a gas-tight sealable chamber 3 is thus provided.

Further, an aqueous liquid in the form of water is provided by the water tank 403.

To provide a substance comprising $Al_4C_3$, a magnesia carbon brick was first prepared from 88.5 by mass of MgO, 8% by mass of C, 2.5% by mass of phenolic resin binder and 1% by mass of Al. To simulate a used condition of this magnesia carbon brick, the magnesia carbon brick was coked for 6 hours at 1,000° C. in a reducing atmosphere, and portions of $Al_4C_3$ formed from portions of the Al and C of the magnesia carbon brick. Portions of the Al in the magnesia carbon brick further reacted with nitrogen from the air during carbonization to form AlN (aluminum nitride). The coked magnesia carbon brick was crushed to a grain size below 1 mm. In this form, the appropriately used magnesia carbon brick crushed to bulk was provided as a substance comprising $Al_4C_3$.

With lid 6 lifted, 10 g of the magnesia carbon brick crushed into bulk material was introduced into chamber 3 of autoclave 2, and chamber 3 was then closed by lid 6. Valve 404 still remained closed during this process.

Valves 104 and 203 were then opened and gaseous nitrogen was introduced from nitrogen tank 103 into chamber 3 through first gas conduit 100, displacing air present in chamber 3 and escaping from chamber 3 through second gas conduit 200. Subsequently, valves 104 and 203 were closed again.

With the valve 404 open, 70 ml of water from the water tank 403 was then introduced into the chamber 3 via the fourth line 400, and the chamber 3 was subsequently sealed gas-tight by closing the valve 404. The stirrer 4 was then activated, so that the crushed magnesia carbon brick located in the chamber 3 and the water located in the chamber 3 were intimately mixed together.

At the same time, the heating device 5 was activated and the chamber 3 was uniformly heated from room temperature to a temperature of 150° C. within a period of 30 minutes and held at this temperature for a period of 5 minutes. After the holding time of 5 minutes at 150° C., the heating device 5 was deactivated and the autoclave 2 was cooled from the outside with water, whereupon the temperature in the chamber 3 dropped again.

During this temperature application to chamber 3 and mixing of the crushed magnesia carbon brick with the water in chamber 3, the $Al_4C_3$ of the magnesia carbon brick reacted with the water according to the following reaction equation (I):

$$Al_4C_3 + 12H_2O \rightarrow 4Al(OH)_3 + 3CH_4 \uparrow \quad (I)$$

Furthermore, the AlN of the magnesia carbon brick and residues of Al unreacted during carbonization reacted with the water according to the following reaction equations (II) and (III):

$$AlN + 3H_2O \rightarrow Al(OH)_3 + NH_3 \uparrow \quad (II)$$

$$2Al + 6H_2O \rightarrow 2Al(OH)_3 + 3H_2 \uparrow \quad (III)$$

Due to the temperature impact on the chamber 3 and the gases methane ($CH_4$), ammonia ($NH_3$) and hydrogen ($H_2$) produced according to the above reaction equations (I) to (III), the nitrogen gas introduced into the chamber 3 and the water vapor produced, the pressure in the chamber 3 increased to about 4 bar overpressure while the magnesia carbon brick and the water reacted with each other.

Before the subsequent opening of valve 203, valve 301 was still opened first and gaseous nitrogen was fed from nitrogen tank 103 through first gas conduit 100 and third gas conduit 300 into second gas conduit 200 to calibrate gas sensor 206 and conductivity detector 207. Gas conditioning pump 205 was activated to support this line of nitrogen gas.

After the temperature in chamber 3 dropped to 45° C., valve 203 was opened to allow the gases (methane, ammonia, hydrogen, water vapor, and nitrogen) located in chamber 3 to be conveyed along the second gas conduit path defined by second gas conduit 200.

To convey these gases located in the chamber 3 along the second gas conduit path defined by the second gas conduit 200, valve 104 was opened and nitrogen was fed from the nitrogen tank 103 via the first gas conduit 100 into the chamber 3. The nitrogen captured the gases located in the chamber 3, left the chamber via the first end 201 of the second gas conduit 200 and, as a carrier gas, subsequently conveyed the gases along the second gas conduit path. The gas volume of the gas conveyed in this process was determined using the flow meter 105. It is true that a portion of the gas present in the chamber 3 already flows into the second gas conduit path when the valve 203 is opened; however, the volume of this gas portion is negligible in relation to the total volume conveyed by the carrier gas, so that the gas volume can be reliably determined by the flow meter 105.

When the gases were conveyed through the bath of 10% sulfuric acid of the gas wash bottle 204, the ammonia was first washed out.

Furthermore, the gases were cooled to 5° C. during their subsequent conveyance through gas processing pump 205, causing water vapor to condense out.

The remaining gases methane, hydrogen and nitrogen were conveyed along the gas sensor 206, and the concentration of methane in the gas was continuously determined by the gas sensor 206.

Subsequently, the remaining gases were conveyed along the conductivity detector 207, with the concentration of hydrogen in the gas being continuously determined by the conductivity detector 207.

Figure 2:
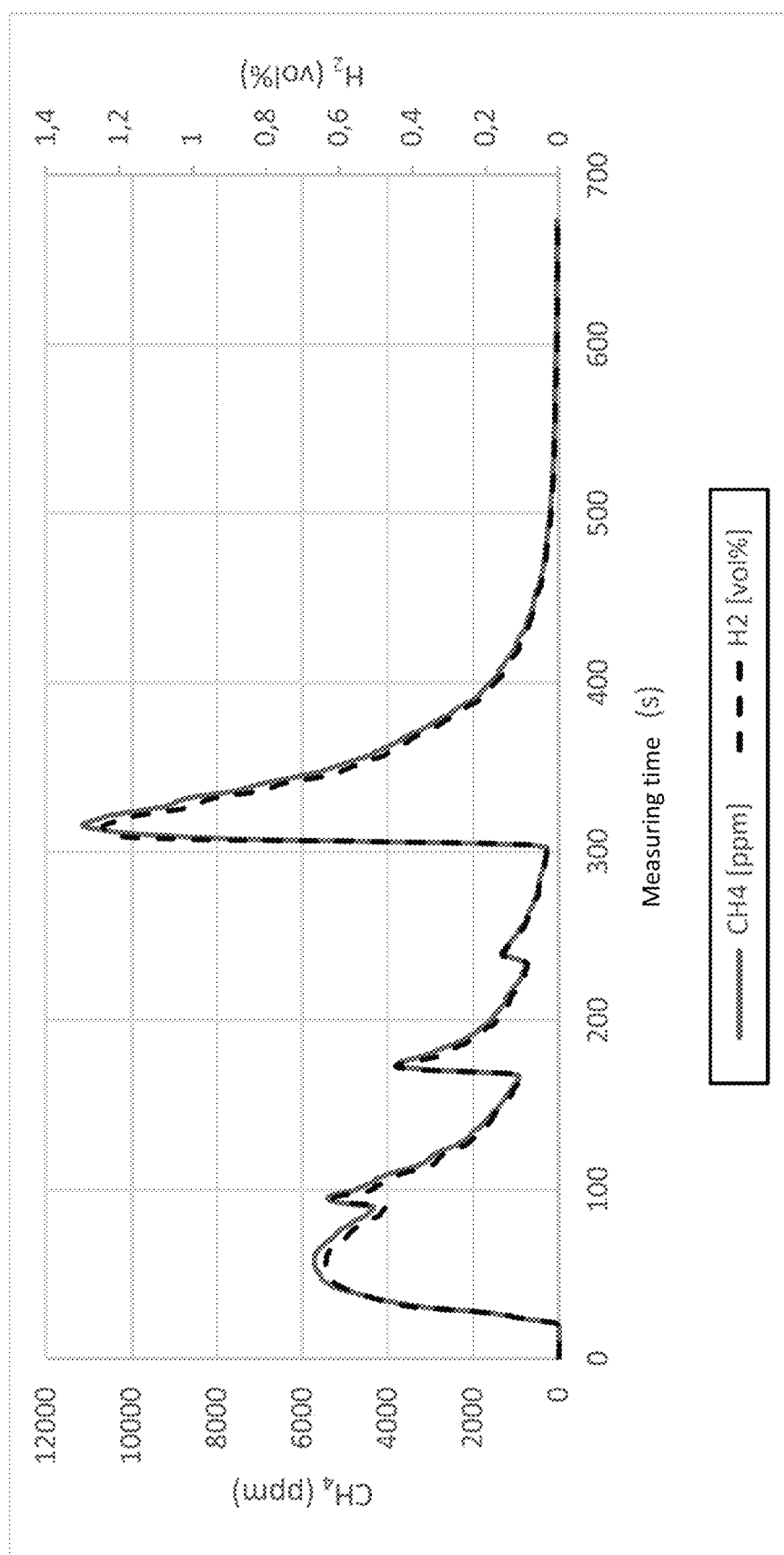
FIG. 2 shows measurement results for the determination of the methane concentration and the hydrogen concentration when carrying out the exemplary embodiment of the method according to the invention.

FIG. 2 shows the results of the measurement of the concentration of methane in ppm determined by the gas sensor 206 and the concentration of hydrogen in % by volume determined by the conductivity detector 207, each over the measurement time in seconds.

Finally, the gases were vented to the outside through the gas vent 208.

Of the gases formed during the reaction of the magnesia carbon brick and the water, methane was quantitatively determined by gas analysis, and then the amount of $Al_4C_3$ in the magnesia carbon brick was quantitatively determined based on this quantitative determination of methane.

First, according to the equation $$V_{(CH4)} [l] = CH_4 [ppm] * 10^{-6} * N_2 [l/min] * 1 [sec]$$

the total volume of the extracted methane was determined.

From the measurement results for the concentration of methane according to FIG. 2, the concentration of methane was first determined over the entire measurement period, which corresponds to the integral over time $\int CH_4 \, dt$. Then the sum of the concentration of methane over the entire measurement period was determined as $CH_4$ [ppm] $= 1.312 * 10^6$ ppm.

Then, from the averaged flow rate over the measurement period of 1.00/60 [l/sec] set at flow meter 105, the total volume of methane pumped was calculated as follows:

$$V_{(CH4)} [l] = 1.312 * 10^6 \text{ ppm} * 10^{-6} * 1.00/60 \text{ [l/sec]} * 1 \text{ [sec]} = 0.022 \text{ [l]}$$

To obtain the amount of substance (in moles) of methane, the calculated volume must be divided by the molar volume of methane under standard conditions. The molar volume under standard conditions is calculated according to the general gas equation $$V_{mol} [l/mol] = (R*T)/p$$

with $R = 8.314 \, [(kg*m^2)/(s^2*mol*K)]$
$T = 223.15 \, [K]$
$p = 101325 \, [Pa] = 101325 \, [kg/(m*s^2)]$ as follows:

$$V_{mol} = (8.314 \ [(kg*m^2)/(s^2*mol*K)]*273.15 \ [K])/101325 \ [kg/(m*s^2)] = 0.022413 \ [m^3/mol] = 22.413 \ [l/mol]$$

The quantitative determination of the amount of methane was finally carried out according to the equation $$n \ CH_4 \ [mol] = V_{(CH4)}[l]/V_{mol}[l/mol]$$

as follows:

$$n \ CH_4 \ [mol] = 0.022 \ [l]/22.413 \ [l/mol] = 9.8*10^{-4} \ [mol]$$

For the subsequent quantitative determination of the amount of substance of $Al_4C_3$ in the magnesia carbon brick was then based on this amount of substance determination for methane according to the reaction equation (I):

$$Al_4C_3 + 12H_2O \rightarrow 4Al(OH)_3 + 3CH_4 \uparrow \qquad (I),$$

after which 1 mole of $Al_4C_3$ reacts to form 3 moles of $CH_4$ (reaction ratio ⅓), calculated back stoichiometrically according to the following equation:

$$Al_4C_3[g] = n \ CH_4 \ [mol]*⅓*M_{(Al4C3)}[g/mol]$$

with

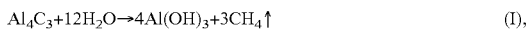

$$M_{(Al4C3)} = \text{molar mass } Al_4C_3 \ [g/mol]$$

This allowed the amount of substance of $Al_4C_3$ in the magnesia carbon brick to be quantitatively determined as follows:

$$Al_4C_3 \ [g] = 9.8*10^{-4} \ [mol]*⅓*143.96 \ [g/mol] = 0.0471 \ g$$

The amount of $Al_4C_3$ in the magnesia carbon brick was thus quantitatively determined to be g.

With respect to the sample amount of 10 g, this corresponded to a concentration of $Al_4C_3$ in the sample magnesia carbon brick of 4710 ppm.

Exemplary Embodiment 2 of the Method

According to a second exemplary embodiment, the method according to the invention was carried out on the apparatus 1 as follows, wherein the quantitative determination of the formed at least one gas, in the exemplary embodiment methane, was carried out by means of a pressure measurement.

The method according to the second exemplary embodiment was carried out essentially according to the method according to exemplary embodiment 1. However, when the method was carried out, during heating of the chamber 3 in the temperature interval of 50 to 85° C. and during cooling of the chamber 3 in the temperature interval of 89 to 50° C., the overpressure was measured by means of the pressure sensor 7. Furthermore, the method was carried out twice, once with the sample according to exemplary embodiment 1 and another time with a magnesia carbon brick ("zero sample"), which differed from the magnesia carbon brick according to embodiment example 1 only in that no Al had been added to it, so that no $Al_4C_3$ could form during its coking.

FIG. 3 shows the measurement results for these pressure measurements. The solid line shows the measurement results for the pressure measurement of the zero sample, while the dashed line shows the measurement results for the pressure measurement of the magnesia carbon brick according to embodiment example 1.

Of the gases formed during the reaction of the magnesia carbon brick and the water, methane was quantitatively determined by means of the pressure measurement in order to subsequently quantitatively determine the amount of $Al_4C_3$ in the magnesia carbon brick based on this quantitative determination of methane.

For this purpose, the overpressure pÜ was first measured with pressure sensor 7 (relative pressure measurement) at 50° C. during heating and during cooling and determined as follows:

$$p_{Ü \ (Heating \ up \ 50° \ C.)} = 0.2745 \ [bar]$$

$$p_{Ü \ (Cooling \ down \ 50° \ C.)} = 0.65 \ [bar]$$

Taking into account a correction factor to account for the expansion of the air, the following is obtained:

$$\text{Correction factor } p \ corr = p_{(zero \ sample \ cooling \ down \ 50° \ C.)} - p_{(zero \ sample \ heating \ up \ 50° \ C.)} = 0.1928 \ [bar] - 0.076 \ [bar] = 0.1168 \ [bar]$$

and thus $$p_{Ü \ (corr \ cooling \ down \ 50° \ C.)} = p_{Ü \ (cooling \ down \ 50° \ C.)} - p_{corr} = 0.65 \ [bar] - 0.1168 \ [bar] = 0.5332 \ [bar]$$

Then the absolute pressure p [bar] was calculated according to:

$$p \ [bar] = p_{ü \ corr} \ [bar] + 1.013 \ [bar]$$

which is therefore $$p_{(absolute \ 50° \ C. \ cooling)} = p_{Ü \ corr} + 1.013 \ [bar] = 0.5332 \ [bar] + 1.013 \ [bar] = 1.5462 \ [bar] = 154620 \ [kg/(m*s^2)]$$

and on cooling $$p_{(absolute \ 50° \ C. \ cooling)} = p_{Ü \ corr} + 1.013 \ [bar] = 0.5332 \ [bar] + 1.013 \ [bar] = 1.5462 \ [bar] = 154620 \ [kg/(m*s^2)]$$

By measuring the hydrogen concentration using the conductivity detector 207 (for measurement results, see FIG. 2), the reaction kinetics could be determined. This allows the assignment of the course of the pressure signal to the reaction products $H_2$ and $CH_4$. This means that the pressure change during heating is mainly due to $H_2$ and during cooling mainly to $CH_4$.

According to the general gas equation $$p*V/(R*T) = n$$

with

Free volume V [l] = 0.1 [l] = 0.0001 $[m^3]$
Density of air $\rho_{air}$ $[kg/m^3]$ = 1.1877 $[kg/m^3]$ = 1.1877 [g/l]
Molar mass air M $M_{air}$ [g/mol] = 28.949 [g/mol]
R = 8.314 $[(kg*m^2)/(s^2*mol*K)]$
$T_{50° \ C.}$ = 273.15 [K] + 50 [K] = 323.15 [K]

with the mass of air $$\text{Mass of air } m_{air} \ [g] = V \ [l]*\rho_{air} = 0.1 \ [l]*1.1827 \ [g/l] = 0.11877 \ [g]$$

and thus the mole of air $$n_{air} \ [mol] = m_{air}/M_{air} = 0.11827 \ [g]/28.949 \ [g/mol] = 0.0041027 \ [mol]$$

results for the mole of hydrogen $$n_{H2 \ (Heating \ up \ 50° \ C.)} = p_{absolute \ (50° \ C. \ heating \ up)}*V/(R*T) - n_{air} = 128750 \ [kg/(m*s^2)]*0.0001 \ [m^3]/(8.314 \ [(kg*m^2)/(s^2*mol*K)]*323.15 \ [K]) - 0.0041027 \ [mol] = 0.00068947 \ [mol].$$

Thus, the amount of substance of methane could be quantitatively determined as follows:

$$n_{CH4\ 50°\ C.}\ [mol] = p_{(absolute\ 50°\ C.\ cooling\ down)} * V/(R*T_{50°\ C.}) - n_{air} - N_{H2\ heating\ up\ 50°\ C.} = 154620\ [kg/(m*s^2)]*0.0001\ [m^3]/(8.314\ [(kg*m^2)/(s^2*mol*K)]*323.15\ [K]) - 0.0041027\ [mol] - 0.00068947\ [mol] = 0.00096291\ [mol].$$

For the subsequent quantitative determination of the amount of substance of $Al_4C_3$ in the magnesia carbon brick, it was then stoichiometrically calculated back on the basis of this substance amount determination for methane according to the reaction equation (I), according to which 1 mol of $Al_4C_3$ reacts to 3 mol of $CH_4$ (reaction ratio ⅓), as follows:

$$Al_4C_3\ [g] = n\ CH_{4\ (50°\ C.)}\ [mol] * ⅓ * M_{(Al4C3)}\ [g/mol] = 9.2691*10^{-4}\ [mol] * ⅓ * 143.96\ [g/mol] = 0.0462\ g$$

The amount of $Al_4C_3$ in the magnesia carbon brick was thus quantitatively determined to be g.

With respect to the sample amount of 10 g, this corresponded to a concentration of $Al_4C_3$ in the sampled magnesia carbon brick of 4620 ppm.

Evaluation of the Quantitative Determination of $Al_4C_3$ According to Embodiments 1 and 2

The embodiment examples 1 and 2 show that the method according to the invention allows a reliable, simple and safe quantitative determination of $Al_4C_3$.

The reliability follows in particular also from a comparison of the results for the determination according to exemplary embodiments 1 and 2, according to which the relative deviation of the measurement results for the quantitative determination on $Al_4C_3$ was only about 1.9%.

The simplicity of the method follows in particular also from the simple performance of the method, in which, among other things, a quantitative determination of the methane does not have to be performed during the entire reaction time due to the reaction in a gas-tight sealed room, as well as the simple quantitative determination of $Al_4C_3$ by means of calculation based on the quantitative determination of the methane.

The safety of the method also results in particular from the use of water for the reaction of the $Al_4C_3$.

What is claimed is:

1. Method for the quantitative determination of $Al_4C_3$, comprising the following steps:
  A. providing a gas-tight sealable autoclave;
  B. providing a substance comprising $Al_4C_3$, wherein the substance comprising $Al_4C_3$ is provided in the form of a refractory product;
  C. providing at least one aqueous liquid that reacts with $Al_4C_3$ to form at least one gas;
  D. placing the substance comprising $Al_4C_3$ and the at least one aqueous liquid in the autoclave;
  E. sealing the autoclave in a gas-tight manner;
  F. reacting the $Al_4C_3$ of the substance comprising $Al_4C_3$ and the at least one aqueous liquid in the autoclave to form the at least one gas, wherein the autoclave is under overpressure during the reaction of the substance comprising $Al_4C_3$ with the at least one aqueous liquid in the autoclave;
  G. quantitatively determining the at least one gas formed; and
  H. quantitatively determining $Al_4C_3$ in the substance comprising $Al_4C_3$ based on the quantitative determination of the at least one gas formed.

2. The method according to claim 1, wherein the at least one gas comprises methane.

3. The method according to claim 1, wherein the at least one aqueous liquid comprises water.

4. The method according to claim 1, wherein the substance comprising $Al_4C_3$ and the at least one aqueous liquid are mixed together.

5. The method according to claim 1, wherein the substance comprising $Al_4C_3$ is carbon bonded.

6. The method according to claim 1, wherein the autoclave is subjected to temperature during the reaction of the substance comprising $Al_4C_3$ with the at least one aqueous liquid in the chamber autoclave.

7. The method according to claim 1, wherein the quantitative determination of the formed at least one gas is performed only after complete reaction of the substance comprising $Al_4C_3$ and the at least one aqueous liquid in the chamber autoclave to form the at least one gas.

8. The method according to claim 1, wherein the at least one gas is quantitatively determined by means of an infrared optical gas sensor.

9. The method according to claim 1, wherein the at least one gas is quantitatively determined by means of a pressure sensor.

* * * * *